(12) United States Patent
Ko et al.

(10) Patent No.: US 10,876,934 B2
(45) Date of Patent: Dec. 29, 2020

(54) PRESS-TYPE WATER SAMPLING DEVICE

(71) Applicant: KOREA WATER RESOURCES CORPORATION, Daejeon (KR)

(72) Inventors: Kwang Myung Ko, Sejong-si (KR); Ki Chul Jang, Namwon-si (KR); Kwan Ju Yang, Mokpo-si (KR); Seung Jae Lee, Jeonju-si (KR)

( * ) Notice: Subject to any disclaimer, the term of this patent is extended or adjusted under 35 U.S.C. 154(b) by 88 days.

(21) Appl. No.: 16/331,639

(22) PCT Filed: Sep. 29, 2017

(86) PCT No.: PCT/KR2017/011050
§ 371 (c)(1),
(2) Date: Mar. 8, 2019

(87) PCT Pub. No.: WO2018/070737
PCT Pub. Date: Apr. 19, 2018

(65) Prior Publication Data
US 2019/0242791 A1    Aug. 8, 2019

(30) Foreign Application Priority Data

Oct. 13, 2016 (KR) .................. 10-2016-0133086

(51) Int. Cl.
*G01N 1/10* (2006.01)
*G01N 1/12* (2006.01)
(Continued)

(52) U.S. Cl.
CPC ............. *G01N 1/10* (2013.01); *E21B 49/083* (2013.01); *G01N 1/12* (2013.01); *G01N 33/18* (2013.01); *G01N 33/1826* (2013.01)

(58) Field of Classification Search
CPC ........... G01N 1/12; G01N 1/14; E21B 49/083
See application file for complete search history.

(56) References Cited

U.S. PATENT DOCUMENTS 3,815,422 A * 6/1974 Niskin ............... G01N 1/12
                                                      73/864.67
5,094,113 A * 3/1992 Wood ................ G01N 1/12
                                                      73/864.67

FOREIGN PATENT DOCUMENTS

JP    02-103439    4/1990
JP    11-023429    1/1999
(Continued)

OTHER PUBLICATIONS

English Specification of 10-1515536.

*Primary Examiner* — Paul M. West
(74) *Attorney, Agent, or Firm* — Antonio Ha & U.S. Patent, LLC

(57) ABSTRACT

The present invention relates to a press-type water sampling device, and to a press-type water sampling device comprising: a water sampling bottle having opened upper and lower parts; and a bumper support, which has a top cap and a bottom cap for blocking the opened upper and lower parts of the water sampling bottle, is formed into a frame having a shape that encompasses the water sampling bottle, and enables the water sampling bottle to be vertically moveable. The present invention enables the water sampling bottle to be separated from the bumper support so as to prevent breakage and water leakage of the water sampling bottle and facilitate cleaning of the water sampling bottle, smoothly collects water at the upper and lower parts of the water sampling bottle since the water sampling bottle is formed at predetermined gaps from the top cap and the bottom cap at the center portion of the bumper support, and can improve accuracy and reliability of a sample water analysis since the water sampling device is formed in an integrated sliding structure, in which the top cap fixed to the bumper support moves down by a messenger moving down when the water sampling device reaches a water depth of a target location (Continued)

and the water sampling bottle is sealed by the top cap and the bottom cap.

8 Claims, 5 Drawing Sheets

(51) Int. Cl.
    *E21B 49/08*     (2006.01)
    *G01N 33/18*     (2006.01)

(56) References Cited

FOREIGN PATENT DOCUMENTS

| | | |
|---|---|---|
| JP | 3181598 | 2/2013 |
| KR | 20-1990-0006587 | 7/1990 |
| KR | 20-0261997 | 2/2002 |
| KR | 20-2011-0003442 | 4/2011 |
| KR | 10-1515536 | 5/2015 |

* cited by examiner

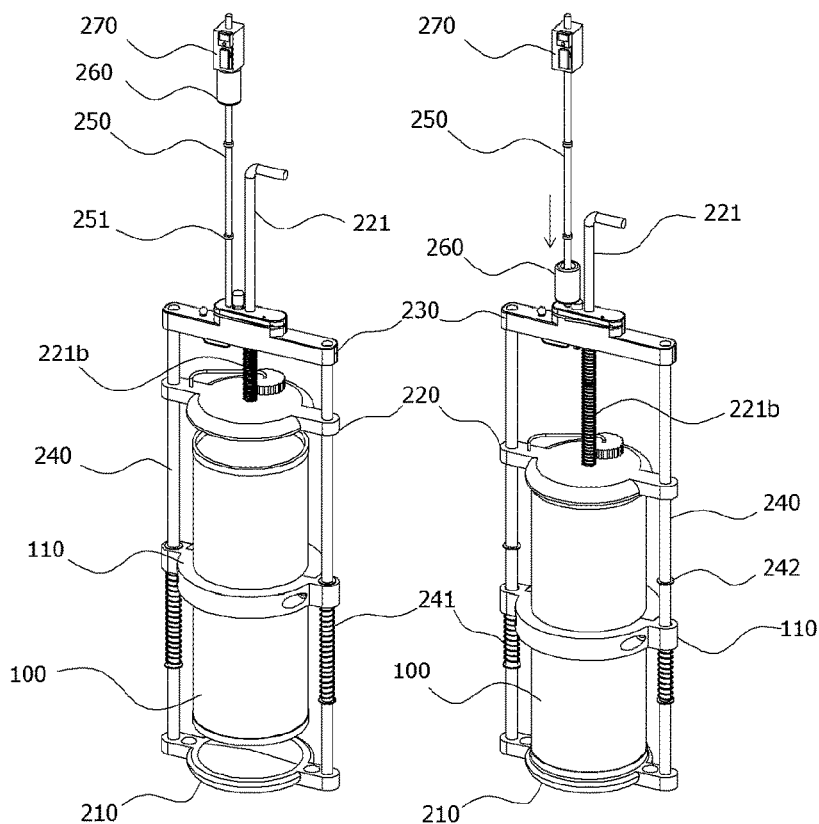
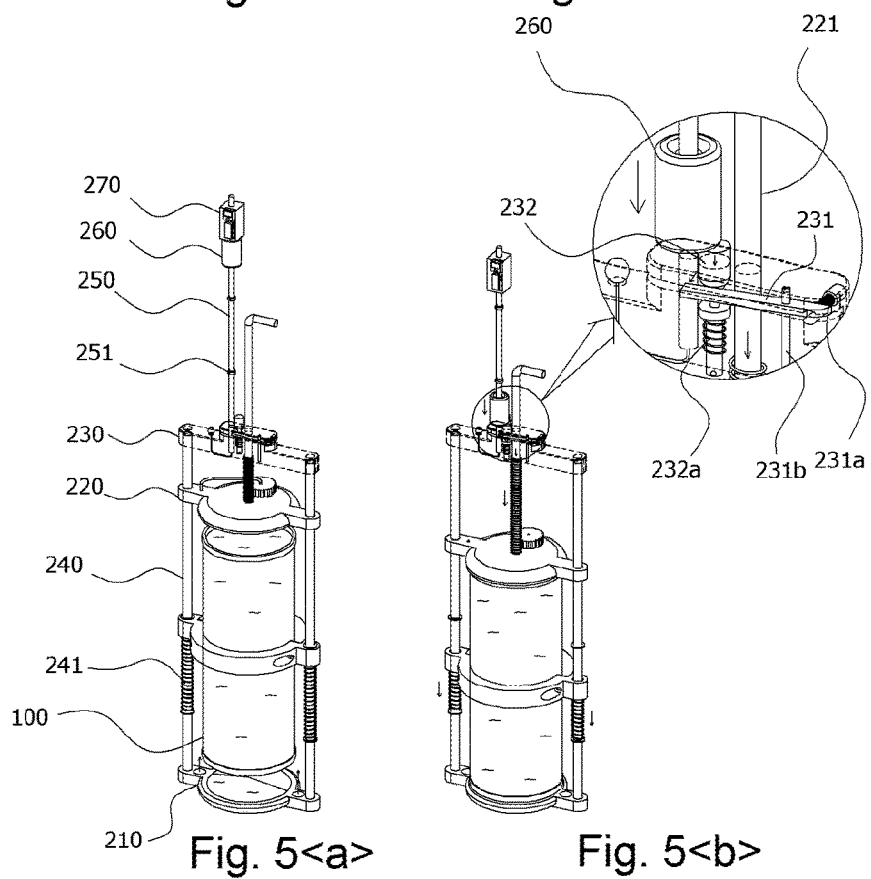

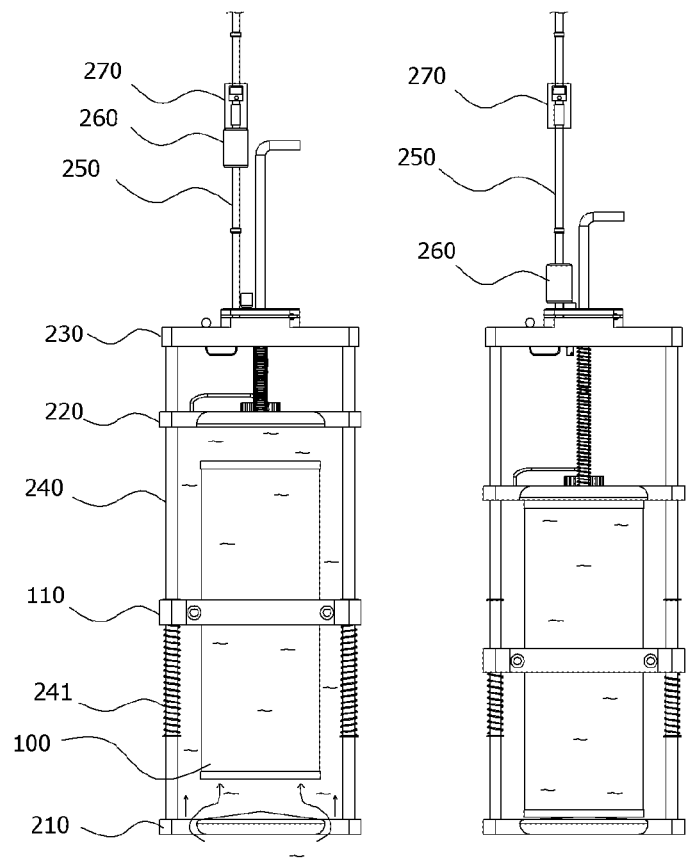
Fig. 6<a>   Fig. 6<b> ns operator*# PRESS-TYPE WATER SAMPLING DEVICE

TECHNICAL FIELD

The present invention relates to a press-type water sampler that may prevent breakage and water leakage from a water collecting container, allow for an easier cleaning of the water collecting container, enable a smooth water collecting through the top and bottom of the water collecting container as the water collecting container is spaced predetermined gaps apart from the top cap and the bottom cap in the center of the bumper support, and enable more reliable and accurate water sampling analysis as it is implemented in a uni-body sliding structure in which a top cap fastened to the bumper support is moved down by a messenger which descends when the water sampler reaches the water depth in the target location, pushing down the water collecting container and thus sealing the water collecting container by the top cap and the bottom cap.

BACKGROUND ART

Water quality tests, as inspecting the physical properties of water or chemical components or microorganisms in water, have been carried out for various purposes, such as selecting water supply sources, inspecting and monitoring purification tasks or contamination of water sources, determining whether tab water meets water quality standards, measuring the degree of contamination of rivers, streams, or sea, or testing the degree of contamination of industrial tab water or sewerage.

Such water quality tests require a sampling of water from a river or sea. To that end, water samplers are used. Various types of water samplers have been developed and are in wide use.

Conventional water samplers typically have a container and a cap connected via a string to the container. When the water sampler reaches a predetermined depth, the string is pulled out, opening the cap and collecting water.

In such a way, however, the water sampler may ascend when the string is pulled out and, thus, an accurate measurement cannot be obtained. Moreover, air sealed off in the container by the cap and the material of the container may render it difficult for the water sampler to reach a desired depth.

Further, conventional water samplers have a uni-body cylindrical water container and thus have difficulty in attaching or detaching parts inside as well as cleaning, repair, or maintenance.

To address such issues, Korean Utility Model Application Publication No. 20-2011-0003442 discloses a separable water sampler which includes a water container including a bottom container and a top container separated from each other and a cap to cover the open top of the water container, wherein parts, e.g., the cap, are easily attachable or detachable inside the water container, and the water sampler is easily cleaned or repaired. However, the water sampler may easily get a foreign body built up inside the water container by its complicated internal structure.

Meanwhile, conventional water samplers may have difficulty in washing out a foreign body buildup inside the water container which may cause an error in water quality analysis. Further, the water container which is formed of glass may easily be broken, causing a failure to seal and collect water. The water depth is identified by marking the rope, connected with the water container, every predetermined length, using, e.g., a marker. This way fails to give an accurate water depth.

PRIOR DOCUMENTS

Patent Documents (Patent Document 1) KR 20-2011-0003442 published on Apr. 6, 2011.
(Patent Document 2) KR 20-0261997 published on Jan. 14, 2002.
(Patent Document 3) KR 20-1990-0006587 published on Jul. 26, 1990.

DETAILED DESCRIPTION OF THE INVENTION

Technical Problem

The present invention has been conceived to address the foregoing problems. An object of the present invention is to provide a press-type water sampler including a water collecting container having an open top and an open bottom to which packings are inserted and a bumper support having a top cap and a bottom cap respectively blocking the top and bottom of the water collecting container, formed as a frame shaped to surround the water collecting container, and installed to allow the water collecting container to be movable up and down and able to increase the durability of the water collecting container, prevent breakage or water leakage of the water collecting container, enable the water collecting container to be removed from the bumper support to allow for an easier cleaning and repair of the water collecting container.

Another object of the present invention is to provide a press-type water sampler in which the water collecting container is fastened in the center of the bumper support while being spaced predetermined gaps apart from the top cap and the bottom cap, enabling smooth water collection through the top and bottom of the water collecting container, the top cap fastened to the bumper support is moved down by the messenger which descends when the water sampler reaches the water depth in the target location, pushing down the water collecting container and thus sealing the water collecting container by the top cap and the bottom cap and, as such, the water sampler is formed in a uni-body sliding structure, allowing for a more reliable and accurate water sampling analysis.

Still another object of the present invention is to provide a press-type water sampler that does not require a separate electric device to move the components for water collection and is thus less likely to be broken while eliminating the hassles of recharging battery or supplying power in the water.

Yet still another object of the present invention is to provide a press-type water sampler in which the knobs are provided at predetermined intervals in the rope tied to the upper frame at the top of the bumper support, the messenger formed as a pendulum and the counter with the limit switch and the gauge board are removably provided in the rope, the water depth may be identified by checking with the gauge board receiving a signal from the limit switch which is stuck to the knob and checks the water depth, at a desired water depth, the messenger may be removed from the counter and be moved down to seal the water collecting container and, thus, water collection may be performed with the water collecting container sealed off.

Technical Solution

To achieve the foregoing objectives, according to the present invention, a press-type water sampler comprises a water collecting container 100 shaped as a cylinder and having an open top and an open bottom and a bumper support 200 including a bottom cap 210 covering the open bottom of the water collecting container 100, a top cap 220 covering the open top, an upper frame 230 having a handle 221 pass therethrough and extend from a top end of the top cap 220, and supplying poles 210 vertically provided between the upper frame 230 and the bottom cap 210. The handle 221 includes a latching hole 221a formed in an upper portion of the handle 221 to allow a latch 231 provided inside the upper frame 230 to be fitted to the latching hole 221a and a second spring 221b positioned under the latching hole 221a and fitted thereover between the upper frame 230 and the top cap 220. A rope 250 along which a messenger 260 formed as a pendulum moves is inserted into an insertion hole 230b formed in the upper frame 230 and on a side of the handle 221. A hammering pin 232 is provided between the handle 221 and the rope 250 to be hit and moved down by the messenger 260 moving down along the rope 250.

According to the present invention, in the bumper support 200, a rim 110 is fastened onto an outer circumferential surface of the water collecting container 100. Both ends of the rim 110 are fitted over the supporting poles 240. The rim 110 is elastically supported by first springs 241 fitted over the supporting poles 240.

According to the present invention, the bottom cap 210 of the bumper support 200 includes a taper having an upper portion projecting upwards more to a center thereof and a lower portion whose diameter decreases downwards. Water is introduced through both sides of the taper.

According to the present invention, the upper frame 230 has a fixing hole 230c for knotting and identifying the rope 250.

According to the present invention, the supplying poles 210 formed on both sides of the bumper support 200 include stepped jaws 242 configured to allow both ends of the rim 110 of the water collecting container 100 to move to a predetermined height.

According to the present invention, an end of the latch 231 is fitted over a shaft 231b vertically passing through the upper frame 230 and an opposite side of a portion of the latch 231 fitted to the latching hole 221a is elastically supported by a third spring 231a. The hammering pin 232 has a tapered portion to contact the latch 231 so that as the hammering pin 232 is moved down by a hitting of the messenger 260, the tapered portion is brought in contact with the latch 231 to horizontally move the latch 231 and escape the latch 231 from the latching hole 221a.

According to the present invention, the rope 250 includes protruding knobs 251 at a predetermined interval. A counter 270 is provided on the messenger 260, the counter 270 including a limit switch 271 and a gauge board 272.

According to the present invention, a fourth spring 232a is provided to a tapered lower portion of the hammering pin 232 to elastically support the hammering pin 232 upwards.

According to the present invention, the handle 221 is formed on the upper frame 230 to bend away from the rope 250.

Advantageous Effects

Therefore, the press-type water sampler according to the present invention may raise the durability of the water collecting container, prevent breakage and water leakage from the water collecting container, and remove the water collecting container from the bumper support to enable easier cleaning and repair of the water collecting container.

Further, according to the present invention, the water collecting container is fastened in the center of the bumper support while being spaced predetermined gaps apart from the top cap and the bottom cap, enabling smooth water collection through the top and bottom of the water collecting container. The top cap fastened to the bumper support is moved down by the messenger which descends upon reaching the water depth in the target location, pushing down the water collecting container and thus sealing the water collecting container by the top cap and the bottom cap. As such, the water sampler is formed in a uni-body sliding structure, allowing for a more reliable and accurate water sampling analysis.

Further, the water sampler of the present invention does not need any electric device and is able to collect water without the need for supplying electricity in the water. Thus, the water sampler may be made compact and be used conveniently.

Further, according to the present invention, the knobs are provided at predetermined intervals in the rope connected with the upper frame at the top of the bumper support. The messenger formed as a pendulum and the counter with the limit switch and the gauge board are removably provided in the rope. The water depth may be identified by checking with the gauge board receiving a signal from the limit switch which is stuck to the knob and checks the water depth. At a desired water depth, the messenger may be removed from the counter and be moved down to seal the water collecting container. Thus, water collection may be performed with the water collecting container sealed off.

Further, according to the present invention, water collection may be performed by dropping the messenger in the location of water collection. Thus, the water sampler may be used in a convenient manner.

BRIEF DESCRIPTION OF DRAWINGS

FIG. 4<a> is a perspective view illustrating a state in which a water collecting container is open according to the present invention;

FIG. 4<b> is a perspective view illustrating a state in which a water collecting container is closed by a top cap and a bottom cap according to the present invention;

FIG. 5<a> is a perspective view illustrating a state in which a water collecting container is open to allow water to be introduced therein according to the present invention;

FIG. 5<b> is a perspective view illustrating a state in which a water collecting container is closed by a top cap and a bottom cap so that water collection is done, according to the present invention;

FIG. 6<a> is a cross-sectional view illustrating a state in which a water collecting container is open to allow water to be introduced therein according to the present invention; and FIG. 6<b> is a cross-sectional view illustrating a state in which a water collecting container is closed by a top cap and a bottom cap so that water collection is done, according to the present invention.

MODE FOR CARRYING OUT THE INVENTION

Hereinafter, preferred embodiments of the present invention are described with reference to the accompanying drawings to be easily practiced by one of ordinary skill in the art.

Figure 1:
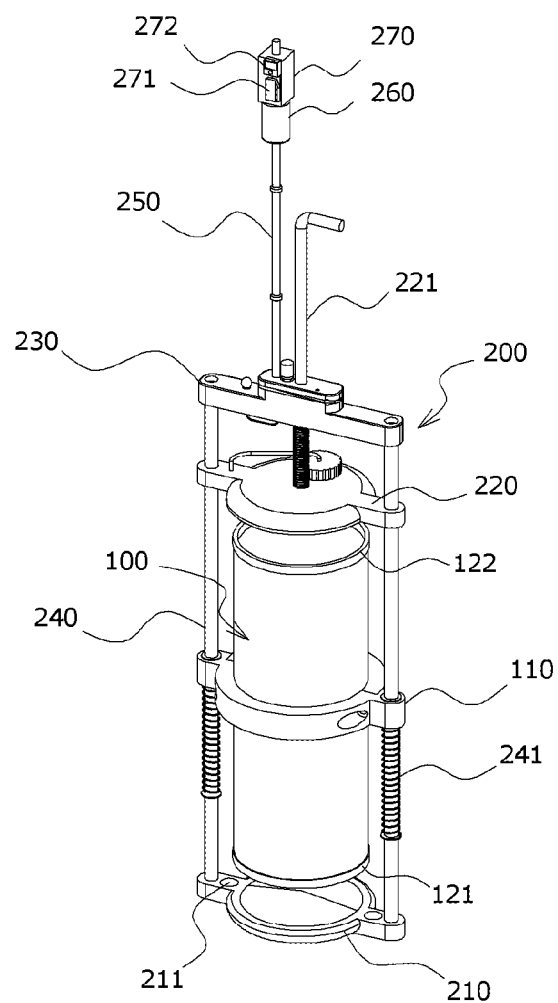
FIG. 1 is an assembled perspective view schematically illustrating a press-type water sampler according to the present invention.
Figure 2:
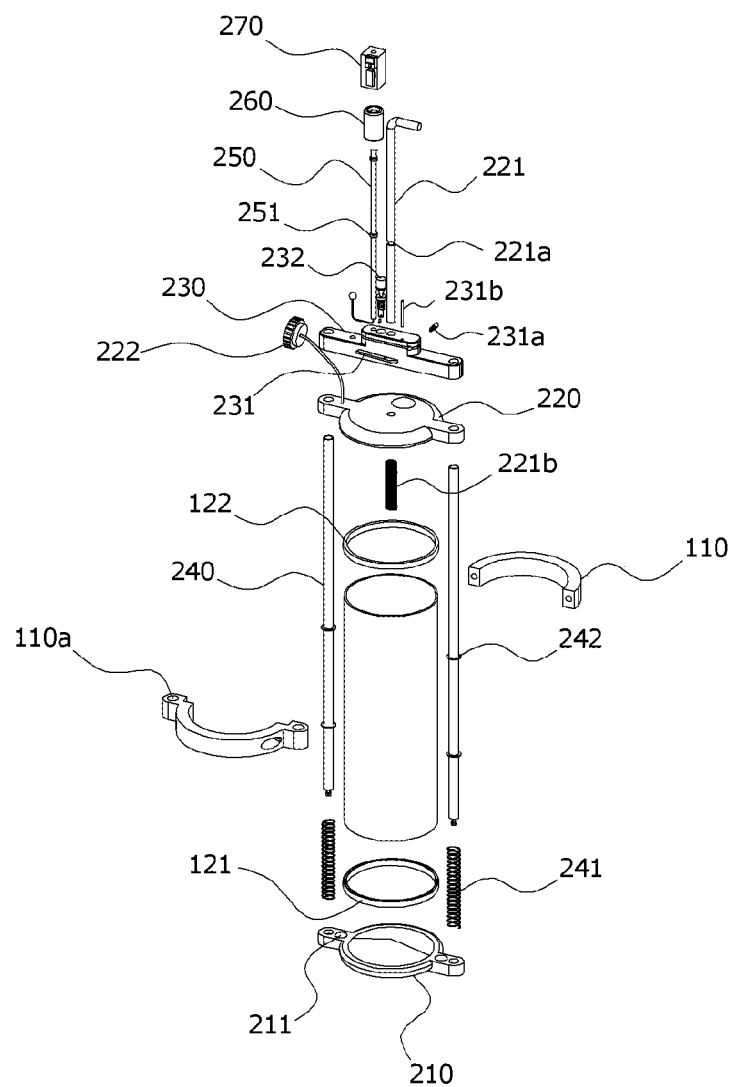
FIG. 2 is an exploded perspective view illustrating a press-type water sampler according to the present invention.
Figure 3:
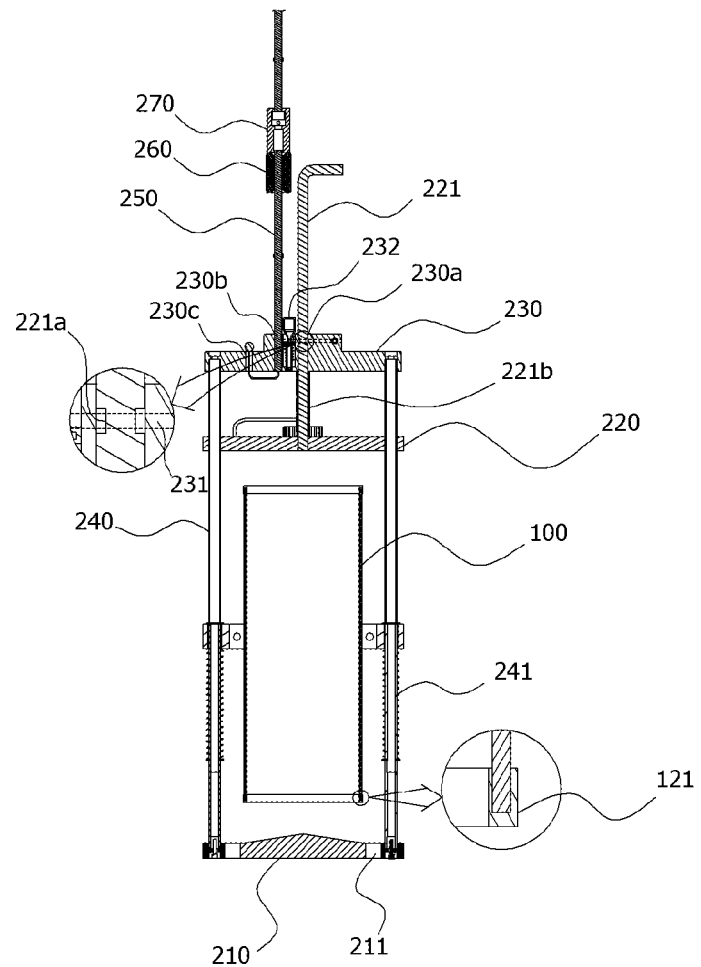
FIG. 3 is a cross-sectional view illustrating a press-type water sampler according to the present invention.

Referring to FIGS. 1 to 6, a press-type water sampler includes a water collecting container 100 shaped as a cylinder with an open top and an open bottom and a bumper support 200 including a bottom cap 210 covering the open bottom of the water collecting container 100 and a top cap 220 covering the open top. An upper frame 230 is provided with a handle 221 formed through the upper frame 230 and extending from a top center of the top cap 220. Two supplying poles 240 are vertically provided between the upper frame 230 and the bottom cap 210. A rim 110, as a frame arranged around the water collecting container 100 by the two supporting poles 240, is fastened onto the outer circumferential surface of the water collecting container 100. Both ends of the rim 110 are fitted over the supporting poles 240. The rim 110 is elastically supported by first springs 241 fitted over the supporting poles 240 and is installed to be able to move up and down the water collecting container 100.

The bottom cap 210 which is circular in shape is provided at the bottom of the bumper support 200 and is tightly connected to the bottom of the water collecting container 100. The top cap 220 which is circular in shape is provided in an upper portion of the bumper support 200 and is tightly connected to the top of the water collecting container 100. The upper frame 230 is provided above the top cap 220.

In the bumper support 200, the supplying poles 210 are installed vertically on both sides of the bottom cap 210 and on both sides of the cylindrical water collecting container 100 and are connected to the upper frame 230, thus forming a frame.

The rim 110 includes two frames which are coupled together on the front and rear surfaces of the water collecting container 100 and around the water collecting container 100.

The frame of the rim 110 which is provided on the front surface of the water collecting container 100 has insertion holes 110a formed vertically through both sides thereof. The supporting poles 240 are inserted through the insertion holes 110a to be able to move up and down. The frames of the rim 100 which are provided on the front and rear surfaces of the water collecting container 100 may have connection holes formed in the respective facing holes thereof, and the frames may be connected together by connecting means, e.g., screws, through the connection holes.

The water collecting container 100 may be removed from the bumper support 200 by disconnecting the front and rear frames of the rim 110 from each other and, thus, be easily washed or repaired.

The water collecting container 100 may be coupled with the supplying poles 210 by the rim 110 to be able to move up and down along the supplying poles 210. The water collecting container 100 may be elastically supported by the first springs 241 provided at the supplying poles 210, and both ends of the rim 110 are moved up to a predetermined height by stepped jaws protruding from the supplying poles 210.

The stepped jaws 242 are positioned at both ends of the rim 110 fitted over the supplying poles 210, restricting the rim 110 from ascending. Lower stepped jaws may be added under the stepped jaws 242, restricting the rim 110 from descending.

The first springs 241 fitted over the supplying poles 210 are disposed under the rim 110 and their movement is restricted to a predetermined distance by lower stepped jaws provided a predetermined interval below the stepped jaws 242 of the supplying poles 210.

The rim 110 is disposed between the stepped jaws 242 and the first springs 241 and is installed to be moved down while pressing the first springs 241.

As the rim 110 is positioned under the stepped jaws 242 of the supplying poles 210 by the elasticity of the first springs 241, the water collecting container 100 is left open in the center of the bumper support 200, and the open top and open bottom of the water collecting container 100 are spaced apart from the top cap 220 and the bottom cap 210 at a predetermined distance, allowing water to smoothly enter or exit through the top and bottom of the water collecting container 100.

The bottom cap 210 includes a taper having a cone-shaped upper portion projecting upwards more to a center thereof and a lower portion whose diameter decreases downwards to allow for quick entrance to or exit from the water collecting container 100 and easier drying. The bottom cap 210 further includes inlet holes 211 on both sides thereof.

When collected, water hits the outer circumferential surface of the tapered-bottom cap 210 under the bottom cap 210 which stops the water path under the water collecting container 100, forming an eddy and resultantly curving and entering the water collecting container 100. A large amount of water may be vertically moved through the inlet holes 211 to the water collecting container 100.

The top cap 220 has a discharge hole to discharge water from the water collecting container 100 and a lid 222 to cover the discharge hole. The lid 222 is connected through a string to the top cap 220, preventing loss.

Meanwhile, placing packings on the top cap 220 and the bottom cap 210 of the bumper support 200 may require holes for the packings. In such case, a foreign body may build up in the holes. Thus, according to the present invention, a first packing 121 and a second packing 122 may be fitted to the top and bottom of the water collecting container 100.

According to the present invention, placing the packings in the water collecting container 100 may eliminate the need for holes in the top cap 220 and the bottom cap 210, thus preventing water leakage and enhancing water tightness.

As such, the first and second packings 121 and 122 fitted to the water collecting container 100 may bring the top and bottom of the water collecting container 100 in tight contact with the top cap 220 and the bottom cap 210 of the bumper support 200, tightly sealing the water collecting container 100.

The upper frame 230 has a center through hole 230a through which the handle 221 is inserted, an insertion hole 230b through which the rope 250 is inserted, and the fixing hole 230c for knotting and identifying the rope 250.

The rope 250 is inserted through the insertion hole 230b of the upper frame 230, pulled out through the fixing hole 230c, and knotted on the top of the upper frame 230. The rope 250 may be firmly secured by the fixing hole 230c, preventing loss of the water sampler.

The second spring 221b is fitted over the handle 221 inserted through the center through hole 230a, elastically supporting the top cap 220 between the upper frame 230 and the top cap 220. The first springs and the second spring may further include a cover (not shown) therearound. The cover may prevent influx of a foreign body or a moss buildup inside the spring.

An end of the handle 221 may be bent away from the rope 250 to allow the messenger 260 from smoothly descending along the rope 250 without being disturbed by the handle 221.

The handle 221 may have a latching hole 221a over the second spring 221b. The latch 231 provided inside the upper frame 230 may be fitted to the latching hole 221a when the handle 221 is pulled up, fastening the handle 221 and the top cap 220 connected with the handle 221.

The second spring 221b is positioned between the upper frame 230 and the top cap 220. The second spring 221b may be contracted when the handle 221 is pulled up so that the latch 231 is stuck to the latching hole 221a and, when the latch 231 is released from the latching hole 221a, is extended to pushing down the top cap 220, sealing the top of the water collecting container 100. The elastic force of the second spring 221b may be set to be much higher than the elastic force of the first springs 241. In other words, as the force of the second spring 221b pushing the top cap 220 is much larger than the force of the first springs 241 holding the water collecting container 100 which is moved down to the bottom cap 210, the force of the second spring 221b strongly pushes the top cap 220 towards the water collecting container 100, allowing the water collecting container 100 to be pushed down to the bottom cap 210 and hence sealing the top and bottom of the water collecting container. The elastic force of the second spring 221b is preferably two or three times larger than the elastic force of the first springs 241.

The latch 231 is shaped as a bar. A shaft 231b vertically formed through the upper frame 230 is inserted through an end of the latch 231 so that the latch 231 is horizontally rotated about the shaft 231b inside the upper frame 230. The latch 231 is pushed out by a third spring 231a disposed at an end thereof and is thus fitted and stuck to the latching hole 221a, so that the handle 221 is not moved down unless an external force is applied.

The hammering pin 232 is positioned between the handle 221 and the rope 250 and is vertically formed through the upper frame 230. An upper portion of the hammering pin 232 projects beyond the top of the upper frame 230. The hammering pin 232 is elastically supported by a fourth spring 232a which is fitted over a lower portion of the hammering pin 232 inside the upper frame 230.

The hammering pin 232 is positioned sufficiently close to the rope 250 and is hit by the messenger that projects from the top of the upper frame 230 and descends along the rope 250. The hammering pin 232 is shaped as a cylinder and has a tapered lower portion whose diameter decreases downwards. The tapered lower portion of the hammering pin 232 has a smaller cylinder. The latch 231 contacts the outer surface of the smaller cylinder of the tapered lower portion of the hammering pin 232. A projecting jaw is formed under the smaller cylinder of the tapered lower portion of the hammering pin 232. The fourth spring 232a is provided under the projecting jaw.

Referring to FIG. 5, as the messenger 260 descends and hits the hammering pin 232, with the latch 231 stuck to the smaller-diameter lower portion of the hammering pin 232, the hammering pin 232 is moved down by the impact, allowing the latch 231 to be pushed out by the larger-diameter portion of the hammering pin 232.

As the latch 231 is released off the latching hole 221a of the handle 221, the handle 221 is quickly moved down by the elastic force of the second spring 221b, so that the top of the water collecting container 100 is covered by the top cap 220, and the water collecting container 100 is moved down, allowing the bottom cap 210 to cover the bottom of the water collecting container 100.

The press-type water sampler of the present invention is dumped into water, with the water sampler clung to the rope 250. The rope 250 has projecting knobs 251 every meter.

The messenger 260 is formed of a pendulum with a predetermined weight. A counter 270 is detachably disposed at the top of the messenger 260.

The counter 270 has a limit switch 271 and a gauge board 272. The limit switch 271 is stuck to the knob 251 of the rope 250 to check the water depth. The gauge board 272 may identify the water depth by a signal received from the limit switch 271.

If the rope 250 is put in the water, the limit switch 271 is stuck to the knob 251 of the rope 250 and sends a signal to the gauge board 272, allowing the user to collect water at the depth in the target location without the need for memorizing how deep the water sampler is placed.

As such, before putting in the water the press-type water sampler of the present invention, the user pulls up the handle 221, which is installed through the center through hole 230a formed in the center of the upper frame 230 which is provided perpendicular to the supplying poles 210 in an upper portion of the bumper support 200, to move up the top cap 220, which is connected with the handle 221 and is installed to be moved up and down along the supplying poles 210. The latch 231 rotatably provided inside the upper chamber 220 is stuck to the latching hole 221a of the handle 221, and the top cap 220 is fastened. The water sampler is put in the water, with the water collecting container 100 open. The user may identify the depth of the water by checking with the counter 270. Where reaching the depth in the target location, the messenger 260 is separated from the counter 270 to be able to descend along the rope 250.

When the press-type water sampler of the present invention reaches the depth in the target location, the messenger 260 is moved down along the rope 250 connected to the upper chamber 220, hitting the hammering pin 232 projecting from the upper chamber 220. The hammering pin 232 descends, pushing out the latch 231 and escaping the latch 231 off the latching hole 221a. Further, the top cap 220 is moved down to push the top of the water collecting container 100, moving the water collecting container 100 down. Thus, the bottom cap 210 covers the bottom of the water collecting container 100. Thus, water sampling can be performed.

Thus, the press-type water sampler of the present invention includes the water collecting container 100 having an open top and an open bottom to which packings are inserted and the bumper support 200 having the bottom cap 210 covering the bottom of the water collecting container 100 and the top cap 220 covering the top of the water collecting container 100, formed as a frame surrounding the water collecting container 100, and installed to allow the water collecting container 100 to move up and down inside the frame. Thus, the water collecting container 100 may have increased durability and be prevented from damage and water leakage. The water collecting container 100 may be removed from the bumper support 200, allowing for easier cleaning and repair.

According to the present invention, the water collecting container 100 may be spaced apart at a predetermined distance from the top cap 220 and the bottom cap 210 while being fastened in the center of the bumper support 200.

Thus, water collection may smoothly be done on the top and bottom of the water collecting container 100. By the messenger 260 which descends upon reaching the depth in the target location, the top cap 220 fastened to the bumper support 200 may be moved down, pushing down the water collecting container 100. Thus, the water collecting container 100 may be sealed by the top cap 220 and the bottom cap 210. Such a uni-body sliding structure may enhance the accuracy and reliability of water sampling analysis.

Further, according to the present invention, the knobs 251 project at a predetermined interval from the rope 250 connected with the upper frame 230 which is positioned at the top of the bumper support 200. The messenger 260 formed of a pendulum and the counter 270 including the limit switch 271 and the gauge board 272 are detachably provided in the rope 250. The depth of water may be identified by checking with the gauge board 272 receiving a signal from the limit switch 271 which is stuck to the know 251 to check the water depth. At a desired water depth, the messenger 260 may be removed from the counter 270 and be moved down, sealing the water collecting container 100. Water sampling may be done with the water collecting container sealed.

Further, in the press-type water sampler of the present invention, the water collecting container 100 which has been done with water sampling may be vertically pulled out the water in an easier manner.

The present invention lacks any configuration that is operated by electrical actions and, thus, is safely and simply operated in the water.

[Description of Symbols]

| | |
|---|---|
| 100: water collecting container | 110: rim |
| 121: first packing | 122: second packing |
| 200: bumper support | 210: bottom cap |
| 211: inlet hole | 220: top cap |
| 221: handle | 221a: latching hole |
| 221b: second spring | 222: lid |
| 230: upper frame | 230a: center through hole |
| 230b: insertion hole | 230c: fixing hole |
| 231: latch | 231a: third spring |
| 231b: shaft | 232: hammering pin |
| 232a: fourth spring | 240: supplying pole |
| 241: first spring | 242: stepped jaw |
| 250: rope | 251: knob |
| 260: messenger | 270: counter |
| 271: limit switch | 272: gauge board |

The invention claimed is:

1. A press-type water sampler comprising:
   a water collecting container (100) shaped as a cylinder and having an open top and an open bottom; and
   a bumper support (200) including a bottom cap (210) covering the open bottom of the water collecting container (100), a top cap (220) covering the open top, an upper frame (230) having a handle (221) pass therethrough and extend from a top end of the top cap (220), and supporting poles (240) vertically provided between the upper frame (230) and the bottom cap (210), wherein the handle (221) includes a latching hole (221a) formed in an upper portion of the handle (221) to allow a latch (231) provided inside the upper frame (230) to be fitted to the latching hole (221a) and a second spring (221b) positioned under the latching hole (221a) and fitted thereover between the upper frame (230) and the top cap (220), wherein a rope (250) along which a messenger (260) formed as a pendulum moves is inserted into an insertion hole (230b) formed in the upper frame (230) and on a side of the handle (221), wherein a hammering pin (232) is provided between the handle (221) and the rope (250) to be hit and moved down by the messenger (260) moving down along the rope (250), wherein a rim (110) is fastened onto an outer circumferential surface of the water collecting container (100), wherein both ends of the rim (110) are fitted over the supporting poles (240), and wherein the rim (110) is elastically supported by first springs (241) fitted over the supporting poles (240).

2. The press-type water sampler of claim 1, wherein the bottom cap (210) of the bumper support (200) includes a taper having an upper portion projecting upwards more to a center thereof and a lower portion whose diameter decreases downwards and inlet holes (211) on both sides of the taper.

3. The press-type water sampler of claim 1, wherein the upper frame (230) has a fixing hole (230c) for knotting and locating the rope (250).

4. The press-type water sampler of claim 1, wherein the supplying poles (210) formed on both sides of the bumper support (200) include stepped jaws (242) configured to allow both ends of the rim (110) of the water collecting container (100) to move to a predetermined height.

5. The press-type water sampler of claim 1, wherein an end of the latch (231) is fitted over a shaft (231b) vertically passing through the upper frame (230) and an opposite side of a portion of the latch (231) fitted to the latching hole (221a) is elastically supported by a third spring (231a), wherein the hammering pin (232) has a tapered portion to contact the latch (231) so that as the hammering pin (232) is moved down by a hitting of the messenger (260), the tapered portion is brought in contact with the latch (231) to horizontally move the latch (231) and escape the latch (231) from the latching hole (221a).

6. The press-type water sampler of claim 1, wherein the rope (250) includes protruding knobs (251) at a predetermined interval, and wherein a counter (270) is provided on the messenger (260), the counter (270) including a limit switch (271) and a gauge board (272).

7. The press-type water sampler of claim 6, wherein a fourth spring (232a) is provided to a tapered lower portion of the hammering pin (232) to elastically support the hammering pin (232) upwards.

8. The press-type water sampler of claim 1, wherein the handle (221) is formed on the upper frame (230) to bend away from the rope (250).

* * * * *